United States Patent
Sajdak et al.

(10) Patent No.: US 9,410,896 B2
(45) Date of Patent: Aug. 9, 2016

(54) METHOD OF MEASUREMENT OF AROMATIC VARNISH APPLICATION

(71) Applicant: RR Donnelley Europe—Sp. z.o.o, Krakow (PL)

(72) Inventors: Marek Sajdak, Krakow (PL); Jaroslaw Plaszczyca, Krakow (PL)

(73) Assignee: RR Donnelley Europe—SP. Z O.O., Krakow (PL)

( * ) Notice: Subject to any disclaimer, the term of this patent is extended or adjusted under 35 U.S.C. 154(b) by 0 days.

(21) Appl. No.: 14/430,006

(22) PCT Filed: Sep. 16, 2013

(86) PCT No.: PCT/PL2013/000117
§ 371 (c)(1),
(2) Date: Mar. 20, 2015

(87) PCT Pub. No.: WO2014/051444
PCT Pub. Date: Apr. 3, 2014

(65) Prior Publication Data
US 2015/0268173 A1      Sep. 24, 2015

(30) Foreign Application Priority Data
Sep. 26, 2012   (PL) .......................................... 400922

(51) Int. Cl.
*G01N 15/02* (2006.01)
*G01N 21/84* (2006.01)
*B41M 3/00* (2006.01)
(52) U.S. Cl.
CPC ........... *G01N 21/8422* (2013.01); *B41M 3/006* (2013.01); *G01N 2021/8427* (2013.01)

(58) Field of Classification Search
CPC .............. B41M 3/006; G01N 21/8422; G01N 2021/8427
USPC ............... 356/335–343; 106/493, 494, 31.28, 106/31.6, 505, 31.86; 101/130
See application file for complete search history.

(56) References Cited

U.S. PATENT DOCUMENTS

| | | | |
|---|---|---|---|
| 8,361,597 B2* | 1/2013 | Shiao | C09C 3/063 106/493 |
| 2004/0009294 A1* | 1/2004 | Kuribayashi | C09D 11/32 427/212 |

(Continued)

FOREIGN PATENT DOCUMENTS

| | | |
|---|---|---|
| JP | S61 172002 A | 8/1986 |
| JP | H11 241912 A | 9/1999 |
| PL | 206460 B1 | 8/2010 |

*Primary Examiner* — Hoa Pham
(74) *Attorney, Agent, or Firm* — Ziegler IP Law Group, LLC

(57) ABSTRACT

A method of measurement of application of aromatic varnish in offset and rotogravure printing includes adding to the aromatic varnish as a marker, one or more of organic and non-organic pigments that can be seen in visible or UV light in the amount ranging from 40,000 to 500,000 per 1 mm$^3$. The mixture of the aromatic varnish and the marker undergoes dispergation, and clean proofs are made where the aromatic varnish coat corresponds to the coat assumed in the printing process. Using a microscope with magnification ranging from 100× to 500×, the number of pigment grains is measured in the clean proofs and then the proper printing process takes place. Samples printed with the varnish are collected and observed under a microscope in the reflected light, and then the number of visible pigment particles in the collected sample is compared with the number of visible pigments in the clean proof.

7 Claims, 1 Drawing Sheet

(56) References Cited

U.S. PATENT DOCUMENTS

2006/0009544 A1* 1/2006 Miyagawa ............ C09D 11/40
523/160

2011/0299098 A1  12/2011 Furuya
2012/0255451 A1* 10/2012 Pineda Domingo ..... B41M 1/06
101/130

* cited by examiner

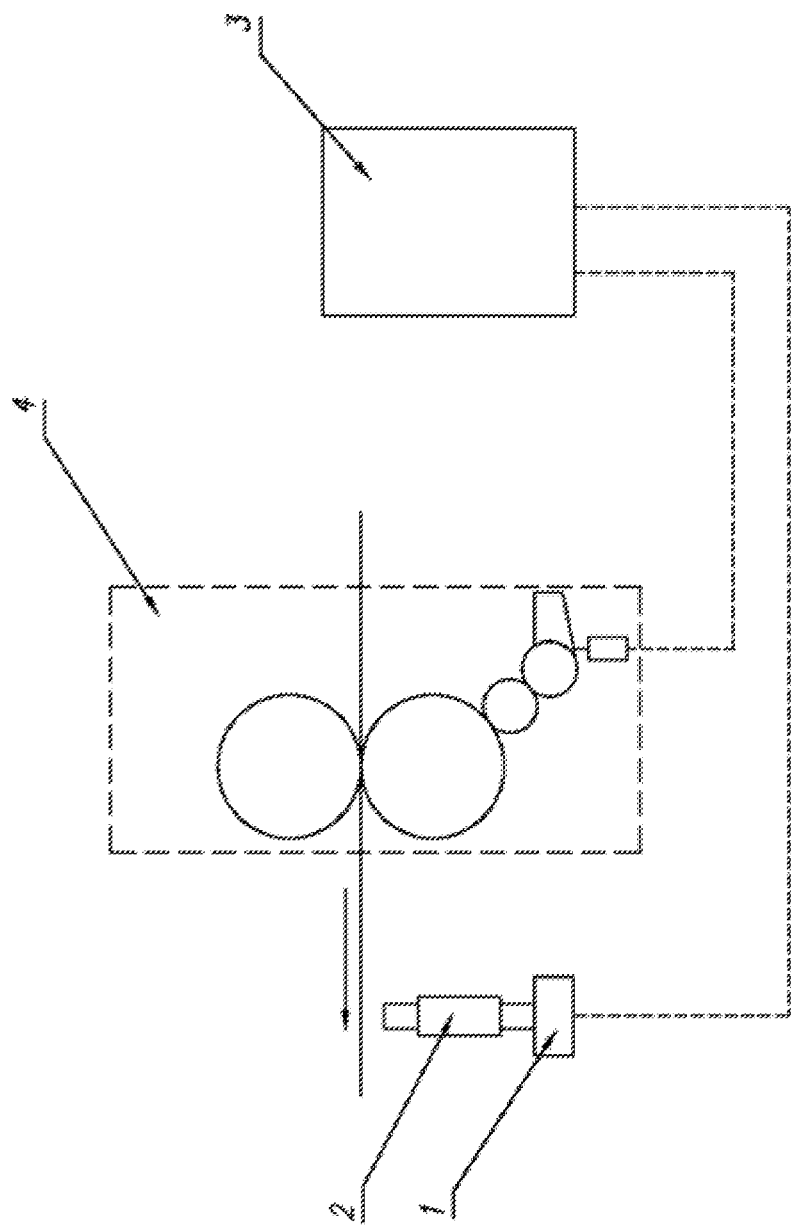

METHOD OF MEASUREMENT OF AROMATIC VARNISH APPLICATION

FIELD

The disclosed embodiments relate to the method of measurement of application of aromatic varnish, in particular clear varnishes used for offset and rotogravure printing.

BRIEF DESCRIPTION OF RELATED DEVELOPMENTS

Recently an important area of printing applications, including offset and rotogravure printing, has been the application of aromatic varnishes. These are printing materials, usually in the form of clear varnish with suspended microcapsules with a diameter of several dozen micrometers. These microcapsules are filled with an aromatic substance. After application of this material on a printing substrate, an almost invisible surface is created which contains microcapsules filled with the aromatic substance. When the capsules are subject to mechanical damage (for example by being rubbed with a hand), the aromatic substance is released, giving a desired aesthetic effect. The very process of application of the aromatic varnish, in particular during printing, consists in subsequent overcoating of the printing substrate with inks and varnishes required in the printing process, while the application of the aromatic clear varnish is the final phase of the printing process.

In the printing process, one of the basic problems of making good aromatic print after the applied printing ink goes dry, is the control of the quantity of the applied printing material per surface measurement unit. It is particularly important in the case of offset printing, where the quantity of the applied ink or varnish may be controlled within a wide range, while at the same time being subject to many external disturbances in the printing process.

There are several prior art methods of control and measurement of the quantity of the applied printing material. These methods consist in the control of the printing materials used in the printing process or in an organoleptic assessment—visual, tactile or aromatic assessment of the aromatic surface. One of the most popular methods is the colorimetric method that involves measurement of the amount of light absorbed by the printed material. However, this method is useless when it comes to the assessment of application of clear printing materials due to their slim ability to absorb light.

A disadvantage of these known methods of measurement is the fact that they can be used only in the printing process to test the quantity of used printing materials in relation to the area of the printed surface, hence such a test can only give a result after a significant area of the surface is overprinted, which usually translates into a large number, i.e. approximately 10,000 copies. The known methods define only the average value of ink or varnish coverage, thus resulting in their insensitivity to the variability of the printing process itself, as well as errors caused by undesired phenomena of the said process, such as for example emulsification, as a result of which the amount of varnish applied to the substrate is smaller than the amount of the used varnish. The known methods lack the possibility to assess the quality of the applied print on the basis of a finished product. The main disadvantages of organoleptic methods involve the subjective nature of the assessment, which makes such methods risky in industrial conditions.

There are also methods of measurement of varnish application through introduction of different types of markers to aromatic varnishes, for example in the form of UV pigment. However, due to the necessity to introduce a considerable number of such markers to varnishes, which leads to significant changes of rheological parameters of the varnish, and in particular its viscosity and mixing of the varnish aroma with the intense aroma of the marker itself, it is very difficult to use this method.

The Polish patent specification No. PL 206460 presents an agent used to identify organic components and compositions in liquid and solid state. This agent contains stylbene derivatives in solid and/or liquid state and optionally carbonic acid diamide, copper in a metallic elemental form or in the form of compounds, rare-earth metal ions showing at the same time Stokes and anti-Stokes emission, dihydric alcohols, ion and/or non-ion surface active agents and higher monohydroxy and trihydroxy alcohols. However the application of the agent specified in patent PL 206460 as a marker is limited only to the determination of structural defects consisting in non-continuity of plastic onto which this agent was applied. It is used also to control the composition and structure and to monitor plastics with different linear and cubical expansion in time and temperature function and after exposure to ultraviolet radiation streams. It is impossible to use this agent as a marker for aromatic varnishes.

SUMMARY

The aim of method of the disclosure is to obtain the correct final effect of printing material applied onto the substrate by applying the appropriate amount of aromatic varnish onto the substrate. In the case of offset printing the average aromatic application considered correct ranges from approx. 1.5 to 2.0 $g/m^2$ and it is considerably higher than a typical application of other transparent printing materials that is considered correct, which is connected with significant technological difficulties. The excess of the applied aromatic varnish does not cause any significant deterioration of product parameters; however it results in excessive use of this varnish, while if the amount of the applied printing material is smaller, the intensity of its aroma is too small.

DETAILED DESCRIPTION OF THE EMBODIMENTS

The essence of the method of measurement of application of aromatic varnish, in particular printing clear varnishes used preferably in the offset and rotogravure printing process according to the invention, consists in the use as a marker of considerably large particles of coloured substances which dispergate in the environment characterised by increased viscosity, i.e. printing aromatic varnishes. Due to the fact that the marker added to the printing varnish is supposed to be invisible to the human eye, it is necessary to use only a small amount of substances as markers compared to varnish volume, which absorb and/or emit radiation beyond the visible spectrum or can be seen only when considerably magnified, preferably more than 100 times. Therefore the substances used as markers in the method specified in the invention preferably have high absorption within the visible spectrum. They are added to the printing varnish in the amount of approx. 0.5% to 10% by weight compared to the clear aromatic varnish. These substances are toxicologically and environmentally safe and dispergate appropriately in varnishes intended for marking. Coloured substances in the form of organic and/or non-organic pigments are used as markers for the needs of measurement of the application of the aromatic varnish in the method specified in the invention. Preferably a coloured substance comprises soot or graphite particles with the grain size ranging from 0.1 μm to 50 μm, preferably with the grain size from 5 μm to 10 μm that can be seen in visible or UV light. The amount of these particles introduced to the varnish, in particular to the aromatic varnish, ranges from approx. 40,000 to 500,000 per 1 mm$^3$, which corresponds to the concentration ranging from 0.5% to 10% per weight, depending on particle material density and particle shape. Due to the size of particles of the pigment introduced to the varnish and concentration of these particles, they can not be seen with a naked eye after application of the varnish on the finished product. The marker introduced to the aromatic varnish in the form of pigment particles is distributed evenly in the entire volume of this varnish through the process of dispergation of the mixture of varnish and marker. The particles of the organic and/or non-organic pigment are added to the varnish during the process of varnish production or during a separate operation by adding to the appropriate volume of the varnish a precisely measured amount of the coloured pigment, and then the mixture of the varnish and pigment undergoes dispergation, preferably with the use of stirrers and/or dispergation equipment, preferably consisting of three cylinders rotating at different speeds. Before starting to print with the aromatic varnish containing particles of the marker specified in the invention, clean proofs are made where the varnish coat corresponds to the coat assumed in the printing process. The amount of visible particles of the pigment is measured in the clean proof. This measurement is made with a microscope 2 with the magnification from 100× to 500×, preferably with an installed counter of marker grains visible in reflected or UV light. The printing process itself with the use of the varnish containing the marker specified in the invention is a standard process. The method of measurement and assessment of the amount of the applied aromatic varnish consists in collection of a sample printed with the varnish during the printing process and observation of this sample under a microscope 2 in the reflected light with a magnification ranging from approx. 100× to 500×. Then the number of pigment particles visible in the collected sample is compared to the number of pigments visible in the clean proof. The comparison is made in the form of a qualitative or quantitative comparison. During the quantitative comparison with the clean proof, pigment particles visible in the visual field of the microscope 2 or any part of this field are counted. Preferably, for the needs of the printing process, in particular offset printing with the use of clear aromatic varnishes, an automated process of measurement of application of the quantity of aromatic varnish is introduced, which consists in the introduction to the system of printing machines of a camera 1 connected to a microscope 2 and a processor 3 which automatically counts marker particles and at the same time compares this amount with a digital clear proof in real time and which also adjusts in real time the quantity of dosed aromatic varnish, depending on measurement results.

The advantage of the method of measurement of the application of the aromatic varnish specified in the invention is a precise determination of the quantity of the varnish applied onto the printed surface. The possibility of preparing varnish with the marker outside the process of varnish production is also advantageous.

The method of measurement of the application of the aromatic varnish specified in the invention is shown in the example of execution.

Example

For the needs of printing of advertising brochures of a cosmetic company, where coats of aromatic varnish were applied to surfaces of different sizes during the last phase of offset printing, a clear aromatic varnish was prepared in the amount of 2 kg.

60 g of the marker consisting of soot particles with the average grain size ranging from approx. 3 to 5 μm were added to 2 kg of the aromatic varnish.

Then the mixture of the varnish and soot particles underwent the process of homogenization in a mixer equipped with slow speed stirrers, the process lasting for a period of 30 minutes.

A mixture of the aromatic varnish and marker was obtained containing 300,000 soot particles in 1 mm$^3$ of varnish, from which, using the IGT Orange Proofer, clean proofs were made with the coverage of 2 g of varnish per m$^2$. The number of markers was measured on clean proofs with the use of a microscope with the magnification of 500×. This measurement showed that the clean proofs had been coated with the varnish containing approx. 630 grains of soot per 1 mm$^2$ of the printed surface.

Then the mixture of the varnish and marker was poured to a dosing device feeding the varnish to the offset printing machine 4 and the process of printing advertising brochures was started. The area covered with the aromatic varnish had a surface of 24 cm$^2$ and the number of proofs was 400,000 items. 2 kg of varnish was used.

As a result of the controlled process of the use of the aromatic varnish, a homogeneous layer of the aromatic print was obtained on all copies of printed advertising brochures, it was 2 g/m$^2$ thick and contained from 580 to 650 grains of the marker per 1 mm$^2$ of the printed surface. Rubbing the print surface covered with aromatic varnish with a finger gave the desired effect of release of the assumed amount of aroma from the varnish.

The invention claimed is:

1. A method of measurement for an application of aromatic varnish including an agent used to identify organic components and compositions in liquid and solid state, comprising:
    adding to the aromatic varnish as a marker, one or more of organic and non-organic pigments that can be seen in visible or UV light in an amount ranging from 40,000 to 500,000 per 1 mm$^3$, which corresponds to a concentration ranging from 0.5% to 10% by weight compared to the aromatic varnish, depending on a density of the pigment added and a shape of grains, the size of which ranges from 0.1 μm to 50 μm, and then the mixture of the aromatic varnish and the marker undergoes dispergation, and
    making clean proofs from the obtained mixture of varnish and marker, where a coat of the aromatic varnish corresponds to a coat assumed in a printing process, and in the clean proofs, a number of pigment grains is microscopically measured with a magnification ranging from approximately 100× to 500×, and
    then the printing process takes place during which samples printed with the varnish during the printing process are collected and microscopically observed under magnification ranging from approximately 100× to 500×, and
    comparing the number of visible pigment particles in the sample collected during the production process to the number of visible pigments in the clean proof.

2. The method according to claim 1, wherein the process of dispergation comprises a stirring process.

3. The method according to claim 1, wherein the size of grains of the pigment, acting as a marker, ranges from 5 μm to 10 μm.

4. The method according to claim 1, wherein the marker comprises soot or graphite particles.

5. The method according to claim 1, wherein the measurement of application of the quantity of aromatic varnish is performed in an automated manner by counting marker particles and at the same time comparing this amount of marker particales with a standard value digital clear proof in real time, and adjusting, also in real time, a quantity of dosed aromatic varnish, depending on measurement results.

6. The method according to claim 1, wherein one or more of the grains of the organic and non-organic pigments are added to the varnish during the process of varnish production or during a separate operation by adding to the appropriate volume of the varnish a precisely measured amount of the coloured pigment, and then the mixture of the varnish and pigment undergoes dispergation.

7. The method according to claim 1, wherein the measurement of application of the quantity of aromatic varnish is performed in an automated manner through introduction to the system of printing machines of a camera connected to a microscope and a processor which automatically counts marker particles and, in real time, a quantity of dosed aromatic varnish depending on the measurement results.

* * * * *